US00PP09544P

United States Patent [19]

Trees

[11] Patent Number: Plant 9,544

[45] Date of Patent: May 7, 1996

[54] GERANIUM PLANT NAMED 'BFP-838 DARK RED'

[75] Inventor: Scott C. Trees, Arroyo Grande, Calif.

[73] Assignee: Geo. J. Ball, Inc., West Chicago, Ill.

[21] Appl. No.: 432,251

[22] Filed: May 10, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

A new and distinct *Pelargonium×hortorum* cultivar named 'BFP-838 Dark Red' is provided. This new Zonal Geranium cultivar was the result of a controlled breeding program wherein a plant designated G4111-4 (non-patented in the United States) was pollinated by the 'Fox' cultivar (U.S. Plant Pat. No. 7,083). The new cultivar forms attractive semi-double dark red florets. Attractive medium green foliage with zonation is well retained during shipment. The growth habit is self-branching and does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-838 Dark Red'.

The new cultivar is a product of a planned breeding program which had the objective of the creation of a new Geranium cultivar that exhibits uniform flowers, medium green foliage, a medium self-branching growth habit that requires no growth regulator, a propensity for rapid rooting, and a stable foliage coloration during shipment.

The breeding program that resulted in the production of the new cultivar of the present invention was carried out in a controlled environment during 1992 at Arroyo Grande, Calif., U.S.A. The female parent (i.e., seed parent) was a plant designated G4111-4 (non-patented in the United States) which exhibits semi-double scarlet florets and medium green foliage. The male parent (i.e., pollen parent) was the 'Fox' cultivar (U.S. Plant Pat. No. 7,083) which exhibits semi-double purple florets with medium green foliage. The parentage of 'BFP-838 Dark Red' cultivar can be summarized as follows:

G4111-4×'Fox'.

The 'BFP-838 Dark Red' cultivar was discovered and selected during 1992 as a highly distinctive flowering plant from among the progeny of the stated cross at Arroyo Grande, Calif., U.S.A. This plant was initially designated BFP-838.

It was found that the new cultivar of the present invention:

(a) exhibits attractive semi-double dark red florets, (b) forms attractive medium green foliage with zonation, and (c) exhibits a medium self-branching growth habit in the absence of a growth regulator.

When plant material of the 'BFP-838 Dark Red' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the 'BFP-838 Dark Red' Cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of characteristics as herein described for the 'BFP-838 Dark Red' cultivar is firmly fixed and is retained through successive generations of such asexual reproduction.

The new 'BFP-838 Dark Red' cultivar has not been observed under all possible environmental conditions. Accordingly, the described phenotype may vary somewhat with variations in the environment, such as temperature, light intensity, and day length.

Of the many commercial cultivars, the 'Sassy Dark Red' cultivar (U.S. Plant Pat. No. 8,053) is considered to be the most similar to the new 'BFP-838 Dark Red' cultivar. When the new cultivar of the present invention is compared to the 'Sassy Dark Red' cultivar, it is found that the 'BFP-838 Dark Red' cultivar exhibits a more compact growth habit (e.g., approximately 24 to 30 cm. in height vs. approximately 31 to 35 cm.), more umbels per plant (e.g., approximately 4 to 5 vs. approximately 3 to 4), and generally has fewer florets per umbel (e.g., approximately 20 to 30 vs. approximately 26 to 36). The florets of the 'BFP-838 Dark Red' cultivar generally has shorter peduncles and shorter internodes as specified in greater detail hereinafter. Additionally, the pedicels of the new cultivar tend to be longer than those of the 'Sassy Dark Red' cultivar.

The new cultivar of the present invention is being marketed by Geo J. Ball, Inc. under the DESIGNER trademark.

BRIEF DESCRIPTION OF THE PHOTOGRAPH

The accompanying photograph of FIG. 1 shows a typical plant of the new 'BFP-838 Dark Red' cultivar with colors generally being as nearly true as it is reasonably possible to make the same in color illustrations of this character. A fully-opened umbel is illustrated together with the contrasting dark green foliage. The plant was being grown in a greenhouse at West Chicago, Ill., U.S.A.

DETAILED DESCRIPTION

Figure 1:
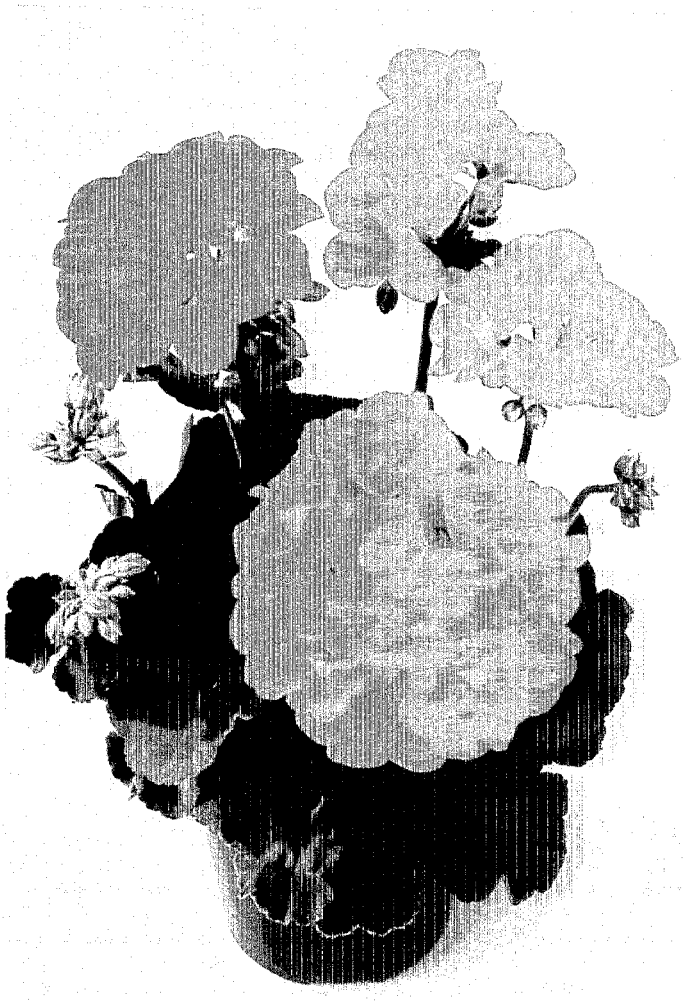

The following observations, measurements and comparisons describe plants grown in Ball FloraPlant's greenhouses at West Chicago, Ill., U.S.A. under greenhouse conditions which approximate those generally used in commercial practice. In the following description, color references are made to the R.H.S. Colour Chart of The Royal Horticultural Society, London, England. The color values were determined between 9:00 and 9:30 a.m. on Dec. 27, 1994, under natural light conditions of 2,000 footcandles.

Classification:

*Botanical.*—*Pelargonium×hortorum* Baily, cv. 'BFP-838 Dark Red'.

*Commercial.*—Zonal Geranium.

Inflorescence

A. Umbel:

*Average diameter.*—Approximately 8.0 to 11.0 cm. compared to approximately 9.0 to 10.5 cm. for the 'Sassy Dark Red' cultivar.

*Average depth.*—Approximately 6.0 to 7.0 cm. compared to approximately 6.0 to 8.5 cm. for the 'Sassy Dark Red' cultivar.

*Peduncle length.*—Approximately 14.5 to 16.0 cm. compared to approximately 16.5 to 22.0 cm. for the 'Sassy Dark Red' cultivar.

*Pedicel length.*—Approximately 2.9 to 5.0 cm. compared to approximately 2.5 to 3.5 cm. for the 'Sassy Dark Red' cultivar.

*Number of umbella plant.*—When grown in a 10.0 cm. pot at 9 weeks after the sticking of a rooted cutting, there commonly are 4 to 5 umbels per plant. This compares to approximately 3 to 4 umbels per plant for the 'Sassy Dark Red' cultivar.

*Number of florets umbel.*—When grown in a 10 cm. pot at 9 weeks after the sticking of a rooted cutting, there commonly are approximately 20 to 30 florets per umbel. This compares to approximately 26 to 36 florets per umbel for the 'Sassy Dark Red' cultivar.

B. Corolla:

*Average diameter.*—Approximately 4.0 to 5.2 cm. compared to approximately 4.5 to 4.6 cm. for the 'Sassy Dark Red' cultivar.

*Form.*—Both the 'BFP-838 Dark Red' cultivar and the 'Sassy Dark Red' cultivar are semi-double with petaloids.

*Number of petaloids.*—Commonly possesses approximately 3 to 5 petaloids per floret. This compares to approximately 1 petaloid per floret for the 'Sassy Dark Red' cultivar.

*Color.*—General tonality from a distance of three meters: Dark red. Adaxial: Red Group 53C. This compares to Red Group 53D for the 'Sassy Dark Red' cultivar. Abaxial: Red Group 47A. This compares to Red Group 52A for the 'Sassy Dark Red' cultivar.

C. Bud:

*Shape.*—Oval-rounded.

*Color.*—Adaxial: Red Group 53C compared to Red Group 53D for the 'Sassy Dark Red' cultivar. Abaxial: Red Group 47A compared to Red Group 52A for the 'Sassy Dark Red' cultivar.

D. Reproductive organs:

*Androecium.*—The anthers are commonly approximately 2 mm. in length. The pollen color for both the 'BFP-838 Dark Red' cultivar and the 'Sassy Dark Red' cultivar is Orange-Red Group 31AQ. The filaments commonly are approximately 11 mm. in length.

*Gynoecium.*—The pistil length commonly is approximately 10 mm. There is a single stigma which commonly has a length of approximately 3.5 mm. which commonly branches into 5 parts, and the style length commonly is approximately 5 mm.

*Fertility.*—Usually does not produce fruits in the absence of mechanical fertilization.

E. Spring flowering response period: Approximately 6 to 7 weeks from rooted cuttings under standard greenhouse conditions.

F. Outdoor flower production: Freely flowering under outdoor growing conditions with substantially continuous blooming.

G. Durability: Ships well.

Plant

A. Foliage: Medium green with zonation.

*Form.*—Reniform, with cordate base.

*Margin.*—Crenate.

*Color.*—Adaxial: Green Group 137B with marginal zone of Green Group 137A. This compares to Green Group 137B with no zonation for the 'Sassy Dark Red' cultivar. Abaxial: Green Group 137C for both the 'BFP-838 Dark Red' cultivar and the 'Sassy Dark Red' cultivar.

*Size.*—Approximately 8.7 to 10.0 cm. at the widest point and approximately 7.6 to 9.2 cm. at the narrowest point. This compares to approximately 8.6 to 8.8 cm. at the widest point and approximately 7.5 to 8.0 cm. at the narrowest point for the 'Sassy Dark Red' cultivar. A medium self-branching growth habit is exhibited in the absence of the use of a growth regulator.

B. General appearance and form:

*Internode length.*—Commonly varies from approximately 1.0 to 1.8 cm. This compares to approximately 1.5 to 2.2 cm. for the 'Sassy Dark Red' cultivar.

*Branching pattern.*—Freely basal branching. No pinching is required to obtain self-branching. A medium self-branching growth habit is exhibited in the absence of the use of a growth regulator.

*Height.*—Approximately 24 to 30 cm. above a 10 cm. pot at 9 weeks under standard greenhouse conditions. This compares to approximately 31 to 35 cm. for the 'Sassy Dark Red' cultivar.

I claim:

1. A new and distinct Geranium plant named 'BFP-838 Dark Red', substantially as herein shown and described, which:

(a) exhibits attractive semi-double dark red florets, (b) forms attractive medium green foliage with zonation, and (c) exhibits a medium self-branching growth habit in the absence of a growth regulator.

* * * * *